United States Patent [19]

Kronenthal

[11] Patent Number: 4,754,041
[45] Date of Patent: Jun. 28, 1988

[54] 3-ACYLAMINO-2-OXO-1-AZETIDINESULFONIC ACIDS

[75] Inventor: David Kronenthal, Yardley, Pa.

[73] Assignee: E. R. Squibb & Sons, Inc., Princeton, N.J.

[21] Appl. No.: 912,877

[22] Filed: Sep. 29, 1986

Related U.S. Application Data

[62] Division of Ser. No. 745,467, Jun. 17, 1985, Pat. No. 4,638,062.

[51] Int. Cl.$^4$ .......................................... C07D 277/40
[52] U.S. Cl. ................................. 548/194; 546/309; 548/128; 548/233; 548/315; 562/439; 562/440
[58] Field of Search ............... 548/194, 128, 233, 315; 546/309; 562/439, 440

[56] References Cited

U.S. PATENT DOCUMENTS 4,599,426 7/1986 Kamiya .................. 548/194

FOREIGN PATENT DOCUMENTS 2071650 9/1981 United Kingdom .............. 548/194

Primary Examiner—Robert Gersil
Attorney, Agent, or Firm—Lawrence S. Levinson; Donald J. Barrack

[57] ABSTRACT

Antibacterial activity is exhibited by 2-azetidinones activated in the 1-position with an —SO$_3$H group and having in the 3-position an acylamino group of the formula

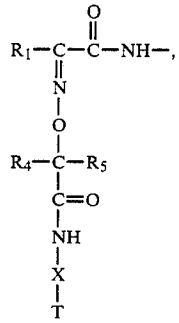

wherein X is —(CH$_2$)$_n$—, n is 0 or 1,

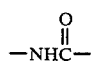

wherein the carbonyl group is bonded to the "T" group, or

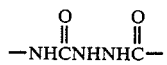

wherein the carbonyl group is bonded to the "T" group and T is

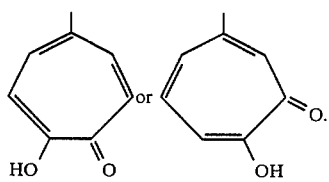

2 Claims, No Drawings

3-ACYLAMINO-2-OXO-1-AZETIDINESULFONIC ACIDS

This is a division of application Ser. No. 745,467, filed June 17, 1985, now U.S. Pat. No. 4,638,062.

BRIEF DESCRIPTION OF THE INVENTION

Compounds having the formula

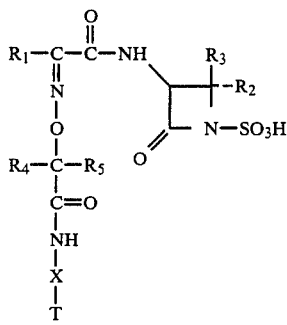

and pharmaceutically acceptable salts thereof, have antibacterial activity. In formula I, and throughout the specification, the symbols are as defined below.

$R_1$ is phenyl, substituted phenyl, 2-amino-4-thiazolyl, 5-amino-3-(1,2,4-thiadiazolyl), 2-amino-4-oxazolyl, 2-amino-4-imidazolyl, or 2-amino-6-pyridyl;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_a$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein $X_1$ is azido, amino (—NH$_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

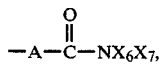

—S—X$_2$, or —O—X$_2$ (wherein A, X$_2$, X$_6$ and X$_7$ are as hereinafter defined)], —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

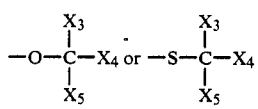

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

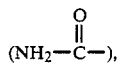

(substituted amino)carbonyl, or cyano (—C≡N)], or

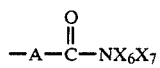

[wherein A is —CH═CH—, —(CH$_2$)$_m$—, —(CH$_2$)$_m$—O—, —(CH$_2$)$_m$—NH—, or —CH$_2$—S—CH$_2$—, m is 0, 1 or 2, and $X_6$ and $X_7$ are the same or different and each is hydrogen, alkyl, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle];

$R_4$ and $R_5$ are the same or different and each is hydrogen or alkyl or $R_4$ and $R_5$ together with the carbon atom to which they are attached are cycloalkyl;

X is —(CH$_2$)$_n$— wherein n is 0 or 1,

wherein the carbonyl group is bonded to the "T" group, or

wherein the carbonyl group is bonded to the "T" group; and

T is

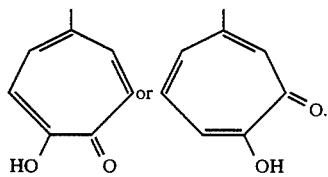

Listed below are definitions of various terms used to describe the β-lactams of this invention. These definitions apply to the terms as they are used throughout the specifications (unless they are otherwise limited in specific instances) either individually or as part of a larger group.

The terms "alkyl" and "alkoxy" refer to both straight and branched chain groups. Those groups having 1 to 10 carbon atoms are preferred.

The term "cycloalkyl" refers to cycloalkyl groups having 3, 4, 5, 6 or 7 carbon atoms.

The term "substituted alkyl" refers to alkyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, $R_a$—oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4, 5, 6 or 7-membered heterocycle" (referred to as "$R_a$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

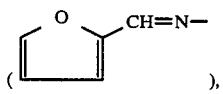

benzylideneamino and substituted alkyl groups (wherein the alkyl group has 1 to 4 carbons). One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy, or amino (—NH$_2$).

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-gluccamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. Of particular interest is the good antipseudomonal activity exhibited by the compounds of this invention. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The compounds of this invention can be prepared by coupling a compound having the formula

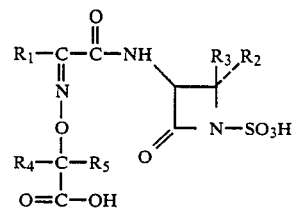

II with a nucleophile having the formula

 III

The coupling reaction can be run using procedures well known in the art. Exemplary of such procedures are the dicyclohexylcarbodiimide coupling and the dicyclohexylcarbodiimide/N-hydroxybenzotriazole coupling.

Alternatively, the compounds of this invention can be prepared by condensing a glyoxylic acid having the formula

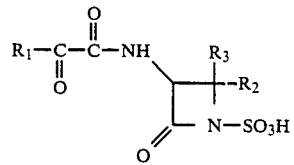

IV with an alkoxylamine having the formula

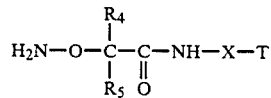

V

The condensation reaction can be run in water, an organic solvent, or a mixed organic solvent-water system.

A third procedure for preparing the compounds of this invention comprises coupling a carboxylic acid having the formula

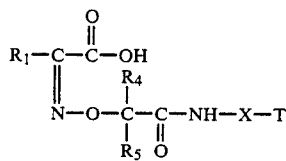   VI with a β-lactam having the formula

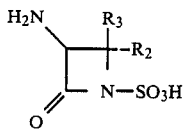   VII

The reaction proceeds most readily if the carboxylic acid is in an activated form. Activated forms of carboxylic acids are well known in the art and include acid halides, acid anhydrides (including mixed anhydrides), activated acid amides and activated acid esters.

The β-lactams of formulas II, IV and VII can be prepared using the methodology described in United Kingdom patent application No. 2,071,650, published Sept. 23, 1981.

A starting material of formula V can be prepared by first reacting a phthalimide having the formula

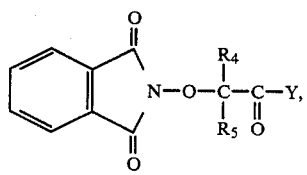   VIII wherein Y is a halogen or hydroxyl group, with a compound of formula III. When Y is hydroxyl, the reaction proceeds best in the presence of a coupling agent such as dicyclohexylcarbodiimide. The phthalimide protecting group is then removed using hydrazine or methylhydrazine. Amine protecting groups other than the phthalimide group can also be used in preparing a compound of formula V.

A carboxylic acid reactant of formula VI can be prepared by reacting a compound having the formula

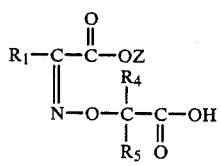   IX with a compound of formula III. Alternatively, a glyoxylic having the formula

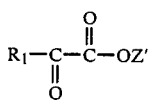   X can be reacted with a compound of formula V to yield the desired reactant of formula VI. As used above, the symbol "Z" represents a carboxylic acid protecting group and "Z'" represents hydrogen or a carboxylic acid protecting group. The carboxylic acids of formula VI are an integral part of this invention.

In the above reactions, if the $R_1$ group contains an amino substituent, it may be protected; exemplary protecting groups are the triphenylmethyl and formyl groups. Additionally, the hydroxyl group of the "T" substituent can also be protected in the above reactions; exemplary protecting groups are the trimethylsilyl, benzyl and benzhydryl groups.

Compounds of formula I, wherein "T" is

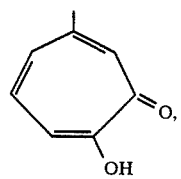

exist as tautomeric mixtures. The two forms are as shown below:

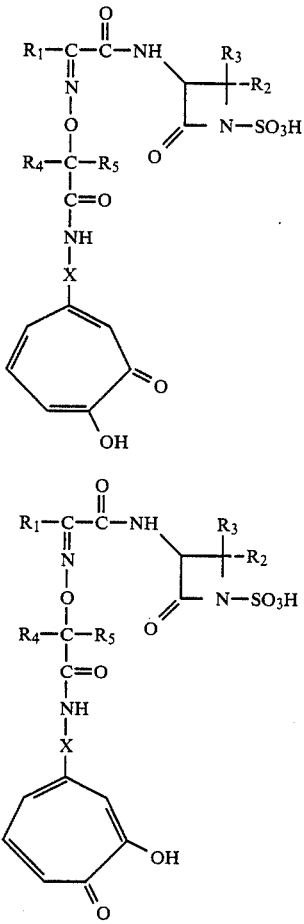

The tautomeric products are obtained in relative amounts that differ from compound to compound. Both forms are included within the scope of structural formula I.

Those compounds of formula I wherein $R_1$ is 2-amino-4-thiazolyl are preferred. In the case of $R_4$ and $R_5$, methyl is the preferred alkyl group.

The compounds of formula I contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

The compounds of formula I have the imino substituent

and can, therefore, exist as the syn or anti isomer or as a mixture of isomers. All of these isomeric forms are within the scope of this invention. In general, however, the syn isomer of a compound of formula I has the greatest activity.

The following examples are specific embodiments of this invention.

EXAMPLE 1

[3S-[3α(Z),4β]]-3-[[(2-Amino-4-thiazolyl)[[2-[(7-hydroxy-1-oxo-1H-2,4,6-cycloheptatrien-4-yl)amino]-1,1-dimethyl-2-oxoethoxy]imino]acetyl]amino]-4-methyl-2-oxo-1-azetidinesulfonic acid

(A)
7-Hydroxy-4-nitroso-1-oxo-1H-2,4,6-cycloheptatriene

A solution of 2-hydroxy-1-oxo-1H-2,4,6-cycloheptatriene (1.5 g, 12.3 mmoles) and sodium nitrite (5 g, 63.3 mmoles) in 150 ml of water was cooled to 0° C. with ice water. Acetic acid (3.62 ml) was added dropwise over 2 minutes. The product precipitated as a yellow-orange solid, and the reaction was stirred for an additional 2 hours. The solid was filtered off, washed with methanol, dried briefly in vacuo and then recrystallized from 40 ml of methanol. The crystals were filtered and washed with cold methanol to yield 0.75 g of orange flakes in the first crop. The mother liquor was concentrated to ~20 ml and a second crop gave an additional 0.30 g.

(B)
4-Amino-7-hydroxy-1-oxo-1H-2,4,6-cycloheptatriene

A suspension of 7-hydroxy-4-nitroso-1-oxo-1H-2,4,6-cycloheptatriene (100 mg, 0.66 mmoles) and platinum oxide (4 mg) in methanol (28 ml) was hydrogenated at room temperature and atmospheric pressure until the calculated amount of hydrogen (30 ml) had been taken up. The yellow solution was then filtered and the filtrate was concentrated in vacuo. Traces of methanol were removed by treatment of the residue with tetrahydrofuran and evaporation. The resulting amine was used in the next step without further purification.

(C)
[3S-[3α(Z),4β]]-3-[[(2-Amino-4-thiazolyl)[[2-[(7-hydroxy-1-oxo-1H-2,4,6-cycloheptatrien-4-yl)amino]-1,1-dimethyl-2-oxoethoxy]imino]acetyl]amino]-4-methyl-2-oxo-1-azetidinesulfonic acid A solution of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid (287 mg, 0.66 mmoles) in dimethylformamide (5 ml) was treated with diisopropylethylamine (133 μl, 0.66 mmoles). 1-Hydroxybenzotriazole hydrate (89.1 mg, 0.66 mmole) and dicyclohexylcarbodiimide (135.9 mg, 0.66 mmoles) were added sequentially and the reaction was stirred at room temperature for 1 hour to produce an active ester. The 5-amino-2-hydroxy-2,4,6-cycloheptatrienone from above was dissolved in 2 ml of dimethylformamide and treated with N-methyl-N-(trimethylsilyl)trifluoroacetamide (501 μl, 2.71 mmoles). The active ester was added via pipet under a stream of nitrogen. The reaction was stirred for ~60 hours at room temperature under argon, treated with 10 ml of ethanol and filtered. The filtrate was concentrated in vacuo and chromatographed on 25 ml of K$^+$ Dowex 50×2—400 ion-exchange resin eluting with 0–10% acetone:water. All the fractions bearing material were combined and lyophilized. The lyophilate was then chromatographed on 100 ml of HP20 resin eluting with 0–5%, 5%–10% and 10%–40% acetone:water and was collected in three fractions to yield a total of 157 mg as a faintly yellow lyophilate.

Analysis Calc'd for $C_{20}H_{21}N_6O_9S_2K.3.2H_2O$:

C, 36.94; H, 4.25; N, 12.92. Found: C, 36.96; H, 3.47; N, 12.80.

EXAMPLE 2

[3S-[3α(Z),4β]]-3-[[(2-Amino-4-thiazolyl)[[2-[[(2-hydroxy-1-oxo-1H-2,4,6-cycloheptatrien-4-yl)carbonyl]hydrazino]-1,1-dimethyl-2-oxoethoxy]imino]acetyl]amino]-4-methyl-2-oxo-1azetidinesulfonic acid

(A)
2-Hydroxy-1-oxo-1H-2,4,6-cycloheptatriene-4-carboxylic acid, hydrazide

Hydrazine hydrate (99%, 5 ml) was added to 2-hydroxy-1-oxo-1H-2,4,6-cycloheptatriene-4-carboxylic acid, methyl ester (1.24 g, 6.9 mmole). The resulting solution was immediately concentrated in vacuo. The red-brown residue was dissolved in water (150 ml) and lyophilized. The lyophilate was dissolved in water (800 ml) and the pH of the solution was adjusted to 4.5 with 1N hydrochloric acid. The resulting mixture was extracted with ethyl acetate (6×1 liter). The combined organic extracts were dried over sodium sulfate and concentrated in vacuo to 900 mg of the title compound.

(B)
[3S-[3α(Z),4β]]-3-[[(2-Amino-4-thiazolyl)[[2-[[(2-hydroxy-1-oxo-1H-2,4,6-cycloheptatrien-4-yl)carbonyl]hydrazino]-1,1-dimethyl-2-oxoethoxy]imino]acetyl]amino]-4-methyl-2-oxo-1-azetidinesulfonic acid Following the procedure of Example 1C, but substituting 2-hydroxy-1-oxo-1H-2,4,6-cycloheptatriene-4-carboxylic acid, hydrazide, for 4-amino-7-hydroxy-1-oxo-1H-2,4,6-cycloheptatriene yields the title compound.

EXAMPLE 3

[3S-[3α(Z),4β]]-3-[[(2-Amino-4-thiazolyl)[[2-[[[[-2-hydroxy-1-oxo-1H-2,4,6-cycloheptatrien-4-yl)carbonyl]hydrazino]carbonyl]hydrazino]-1,1-dimethyl-2-oxoethoxy]imino]acetyl]amino]-4-methyl-2-oxo-1-azetidinesulfonic acid

(A)

2-Hydroxy-1-oxo-1H-2,4,6-cycloheptatriene-4-carboxylic acid, 2-(hydrazinocarbonyl)hydrazide, hydrochloride A mixture of 2-hydroxy-1-oxo-1H-2,4,6-cycloheptatriene-4-carboxylic acid, hydrazide (1 g) and N-methyl-N-(trimethylsilyl)trifluoroacetamide (3.5 g) in acetonitrile is stirred at 50° C. for 1 hour and treated with 2-benzyloxycarbonylhydrazine carbonyl chloride (Chem. Ber. 97 2551 (1964)). After stirring overnight, the solvent is removed and the residue is dissolved in acetic acid, treated with hydrogen chloride gas and stirred at 70° C. overnight. After removing the solvent, ether is added forming a precipitate of the title compound.

(B)

[3S-[3α(Z),4β]]-3-[[(2-Amino-4-thiazolyl)[[2-[[[[-(2-hydroxy-1-oxo-1H-2,4,6-cycloheptatrien-4-yl)carbonyl]hydrazino]carbonyl]hydrazino]-1,1-dimethyl-2-oxoethoxy]imino]acetyl]amino]-4-methyl-2-oxo-1-azetidinesulfonic acid Following the procedure of Example 1C, but substituting 2-hydroxy-1-oxo-1H-2,4,6-cycloheptatriene-4-carboxylic acid, 2-(hydrazinocarbonyl)hydrazide, hydrochloride for 4-amino-7-hydroxy-1-oxo-1H-2,4,6-cycloheptatriene and adding one equivalent of diisopropylamine immediately prior to adding the N-methyl-N-(trimethylsilyl)trifluoroacetamide, yields the title compound.

EXAMPLE 4

[3S-[3α(Z),4β]]-3-[[(2-Amino-4-thiazolyl)[[2-[[(7-hydroxy-1-oxo-1H-2,4,6-cycloheptatrien-4-yl)carbonyl]hydrazino]-1,1-dimethyl-2-oxoethoxy]imino]acetyl]amino]-4-methyl-2-oxo-1-azetidinesulfonic acid

(A)

7-Hydroxy-1-oxo-1H-2,4,6-cycloheptatriene-4-carboxylic acid, ethyl ester

A mixture of 7-hydroxy-1-oxo-1H-2,4,6-cycloheptatriene-4-carboxylic acid (J. Chem. Soc. 1954, 530) in ethanolic hydrogen chloride is refluxed, cooled and concentrated. The residue is treated with ethyl acetate, filtered and evaporated to afford the title compound.

(B)

7-Hydroxy-1-oxo-1H-2,4,6-cycloheptatriene-4-carboxylic acid, hydrazide

Following the procedure of Example 2A, but substituting 7-hydroxy-1-oxo-1H-2,4,6-cycloheptatriene-4-carboxylic acid, ethyl ester for 2-hydroxy-1-oxo-1H-2,4,6-cycloheptatriene-4-carboxylic acid, methyl ester, yields the title compound.

(C)

[3S-[3α(Z),4β]]-3-[[(2-Amino-4-thiazolyl)[2-[[(7-hydroxy-1-oxo-1H-2,4,6-cycloheptatrien-4-yl)carbonyl]hydrazino]-1,1-dimethyl-2-oxoethoxy]imino]acetyl]amino]-4-methyl-2-oxo-1-azetidinesulfonic acid Following the procedure of Example 1C, but substituting 7-hydroxy-1-oxo-1H-2,4,6-cycloheptatriene-4-carboxylic acid, hydrazide for 4-amino-7-hydroxy-1-oxo-1H-2,4,6cycloheptatriene yields the title compound.

EXAMPLE 5

[3S-[3α(Z),4β]]-3-[[(2-Amino-4-thiazolyl)[[2-[[[[(-7-hydroxy-1-oxo-1H-2,4,6-cycloheptatrien-4-yl)carbonyl]hydrazino]carbonyl]hydrazino]-1,1-dimethyl-2-oxoethoxy]imino]acetyl]amino]-4-methyl-2-oxo-1azetidinesulfonic acid

(A)

7-Hydroxy-1-oxo-1H-2,4,6-cycloheptatriene-4-carboxylic acid, 2-(hydrazinecarbonyl)hydrazide Following the procedure of Example 3A, but substituting 7-hydroxy-1-oxo-1H-2,4,6-cycloheptatriene-4-carboxylic acid, hydrazide for 2-hydroxy-1-oxo-1H-2,4,6-cycloheptatriene-4-carboxylic acid, hydrazide, yields the title compound.

(B)

[3S-[3α(Z),4β]]-3-[[(2-Amino-4-thiazolyl)[[(2-[[[[-(7-hydroxy-1-oxo-1H-2,4,6-cycloheptatrien-4-yl)carbonyl]hydrazino]carbonyl]hydrazino]-1,1-dimethyl-2-oxoethoxy]imino]acetyl]amino]-4-methyl-2-oxo-1-azetidinesulfonic acid Following the procedure of Example 1C, but substituting 7-hydroxy-1-oxo-1H-2,4,6-cycloheptatriene-4-carboxylic acid, 2-(hydrazinecarbonyl)hydrazide for 4-amino-7-hydroxy-1-oxo-1H-2,4,6-cycloheptatriene and adding one equivalent of diisopropylamine immediately prior to adding the N-methyl-N-(trimethylsilyl)-trifluoroacetamide, yields the title compound.

What is claimed is:

1. A compound having the formula $$\begin{array}{c} \text{O} \\ \parallel \\ R_1-C-C-OH \\ \parallel \quad R_4 \\ N-O-C-C-NH-X-T \\ \mid \quad \parallel \\ R_5 \quad O \end{array}$$

wherein $R_1$ is phenyl, substituted phenyl, 2-amino-4-thiazolyl, 5-amino-3(1,2,4thiadiazolyl), 2-amino-4-oxazolyl, 2-amino-4-imidazolyl, or 2-amino-6-pyridyl;

$R_4$ and $R_5$ are the same or different and each is hydrogen or alkyl, or $R_4$ and $R_5$ together with the carbon atom to which they are attached are cycloalkyl;

X is $-(CH_2)_n-$ wherein n is 0 or 1, $$\begin{array}{ccc} \text{O} & \text{O} & \text{O} \\ \parallel & \parallel & \parallel \\ -\text{NHC}- & \text{or} & -\text{NHCNHNHC}-; \text{ and} \end{array}$$

T is 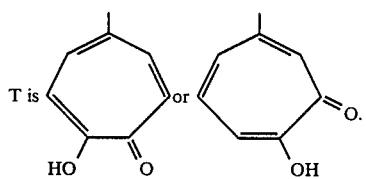

wherein the terms "alkyl" and "alkoxy" refer to groups having 1 to 10 carbon atoms;
the term "cycloalkyl" refers to groups having 3, 4, 5, 6 or 7 carbon atoms; and
the term "substituted phenyl" refers to a phenyl group substituted with 1, 2 or 3 amino, halogen, hydroxyl, trifluoromethyl, alkyl of 1 to 4 carbons, alkoxy of 1 to 4 carbons, alkanoyloxy, aminocarbonyl, or carboxy groups.

2. A compound in accordance with claim 1 wherein $R_1$ is 2-amino-4-thiazolyl.

* * * * *